US00PP35122P2

(12) United States Plant Patent
Bergman

(10) Patent No.: US PP35,122 P2
(45) Date of Patent: Apr. 25, 2023

(54) ***MANDEVILLA* PLANT NAMED 'MANZ0023'**

(50) Latin Name: ***Mandevilla sanderi* (Hemsl.) Woodson**
Varietal Denomination: MANZ0023

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/889,490

(22) Filed: Aug. 17, 2022

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./226, 232
See application file for complete search history.

*Primary Examiner* — Susan McCormick Ewoldt
(74) *Attorney, Agent, or Firm* — Dale Skalla

(57) ABSTRACT

A new *Mandevilla* plant named 'MANZ0023', particularly distinguished by its large red nonfading flowers, glossy and smooth dark green foliage, bushy plant habit with a tendency to produce vines under low light growing conditions and with excellent branching and flower production and fast flowering response.

1 Drawing Sheet

Latin name of the genus and species of the plant claimed: *Mandevilla sanderi* (Hemsl.) Woodson.

Varietal denomination: 'MANZ0023'.

BACKGROUND OF THE NEW PLANT

The present invention comprises a new *Mandevilla*, botanically known as *Mandevilla sanderi*, and hereinafter referred to by the variety name 'MANZ0023'.

'MANZ0023' is a product of a planned breeding program. The new cultivar is particularly distinguished by large red nonfading flowers, glossy and smooth dark green foliage, bushy plant habit with a tendency to produce vines under low light growing conditions and with excellent branching and flower production and fast flowering response.

'MANZ0023' originates from a hybridization made in a controlled breeding program in Amatitlan, Guatemala. The pollinations were made in 2013.

The female parent was an unpatented, proprietary plant identified as 'DIP-252' and having very large red flowers, a more vigorous and strong vining habit and slower flowering response.

The male parent of 'MANZ0023' was an unpatented, proprietary plant identified as 'DIP-059', with a smaller dark red flower color, less vigorous non-vining plant habit and smaller foliage.

The resulting seeds were sown in March 2015 and 'MANZ0023' was selected as one flowering plant within the progeny of the stated cross in January 2016 in a greenhouse in Gilroy, Calif.

The first act of asexual reproduction of 'MANZ0023' was accomplished when vegetative stem cuttings were propagated from the initial selection in March 2016 in a controlled environment in Gilroy, Calif.

BRIEF SUMMARY OF INVENTION

Horticultural examination of plants grown from cuttings of the plant initiated in May 2017 in Gilroy, Calif., and continuing thereafter, has demonstrated that the combination of characteristics as herein disclosed for 'MANZ0023' are firmly fixed and are retained through successive generations of asexual reproduction.

'MANZ0023' has not been observed under all possible environmental conditions. The phenotype may vary significantly with variations in environment such as temperature, light intensity and day length.

A Plant Breeder's Right for this cultivar has not yet been applied for. 'MANZ0023' has not been made publicly available prior to the effective filing date of this application, notwithstanding any disclosure that may have been made less than one year prior to the effective filing date of this application by the inventor or another who obtained 'MANZ0023' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

The accompanying photographic drawings show typical flower and foliage characteristics of 'MANZ0023' with colors being as true as possible with an illustration of this type.

Figure 1:
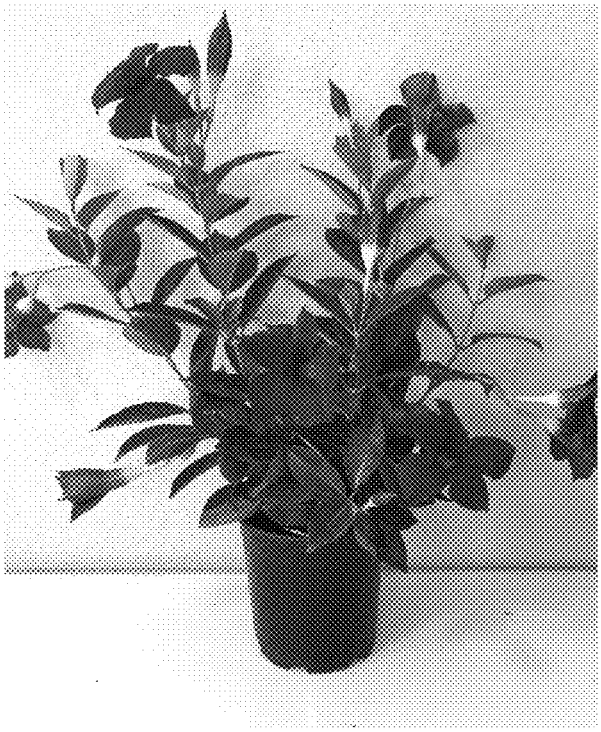
Figure 2:
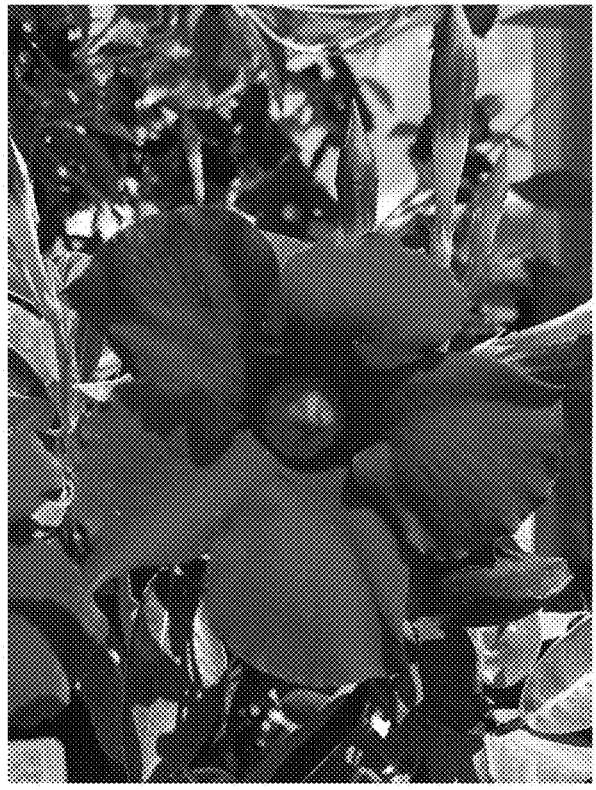

The photographic drawings show in FIG. 1, a flowering potted plant of the new variety and in FIG. 2, a close-up of the flower.

DETAILED BOTANICAL DESCRIPTION

The aforementioned photographs were taken in July 2022 in Gilroy, Calif. The plant was grown in a quart size pot outdoors and was about 6 months in age.

TABLE 1

DIFFERENCES BETWEEN THE NEW VARIETY 'MANZ0023' AND A SIMILAR VARIETY

| | 'MANZ0023' | 'FISRIX DERED', U.S. Plant Pat. No. 20,714 |
|---|---|---|
| Flower size: | Larger | Smaller |
| Foliage color: | Darker | Lighter |
| Flower color: | Resists fading | Fades easily |

Plant:

*Form, growth, and habit.*—Perennial or sub-shrub, herbaceous younger stems, woody at base of older stems, semi-upright, with moderate tendency of developing vines depending on season and light intensity. Time for producing a commercial, flowering plant approximately is 16 weeks for one plant in a quart size container.

*Plant height.*—30 cm.

*Plant height (inflorescence included).*—36 cm.

*Plant width.*—35 cm.

Roots:

*Number of days to initiate roots.*—About 16-20 days at about 22 degrees C.

*Number of days to produce a rooted cutting plant.*—5 weeks at about 22 degrees C.

*Type.*—Fibrous, a little fleshy, free branching.

*Color.*—RHS 155D.

Foliage:

*Arrangement of leaves.*—Simple leaf, opposite and decussate.

*Immature leaf, color upper surface.*—Closest to RHS 138A.

*Immature leaf, color lower surface.*—Closest to RHS 138B.

*Mature leaf, color upper surface.*—RHS 139A.

*Mature leaf, color lower surface.*—RHS 137B.

*Length.*—6.5-8.5 cm.

*Width.*—3.3-4.6 cm.

*Shape.*—Ovate.

*Base shape.*—Rounded.

*Apex shape.*—Apiculate.

*Margin.*—Entire.

*Texture, upper surface.*—Smooth, glossy, glabrous.

*Texture, lower surface.*—Smooth, glossy, glabrous.

*Pattern of leaf veins.*—Pinnate.

*Color of veins, upper surface.*—RHS 137C.

*Color of vein (midrib), lower surface.*—RHS 139D.

*Petiole color.*—RHS 137C.

*Length.*—0.8-1.1 cm.

*Diameter.*—0.2-0.25 cm.

*Petiole, texture.*—Glabrous.

Stem:

*Branching characteristics.*—Moderately free branching.

*Quantity of main branches per plant.*—4-5.

*Color of stem.*—RHS 144A.

*Length of stem.*—22-27 cm.

*Diameter (at about mid-point).*—0.3 cm.

*Length of internodes.*—2.1-4.8 cm.

*Stem, texture.*—Smooth and glabrous.

Inflorescence:

*Type of inflorescence.*—Raceme of several flowers, emerging from nodes of the stem.

*Number of flowers per inflorescence.*—4-5.

*Blooming habit.*—Continuously through the summer months.

*Quantity of flowers per plant.*—About 10 in various stages of development.

*Lastingness of individual blooms on the plant.*—Approximately 8-10 days, depending on temperature.

*Fragrance.*—Absent.

Peduncle

*Color.*—Green, RHS 144B, some anthocyanins present.

*Length .*—1.7-2.2 cm.

*Diameter.*—0.2-0.25 cm.

*Texture.*—Smooth, glabrous, somewhat glossy.

Bud (just before opening/showing color):

*Color.*—Closest to RHS 187A with tones of 185B.

*Length.*—7.6 cm.

*Width.*—1.7 cm.

*Shape.*—Elongated, spindle shape.

Immature flower:

*Diameter.*—7.8 cm.

*Vertical diameter.*—About 7.8 cm.

*Color upper surface.*—RHS 146A.

*Color lower surface.*—RHS 185A.

Mature flower:

*Shape.*—Funnelform, funnel shaped base, formed by 5 partly fused petals, with the petal lobes opening outwards, and a little overlapping.

*Flower, horizontal diameter.*—8.5 cm.

*Flower, vertical diameter.*—About 6.0 cm.

*Flower, diameter of the funnel.*—1.6 cm.

*Flower color, general.*—Red.

*Flower color, upper surface.*—Closest to RHS 185A.

*Flower color, lower surface.*—Closest to RHS 187B.

*Color of the funnel, inner side.*—Closest to RHS 169B.

*Color of the funnel, outside.*—RHS 185B and 158C.

*Petal, shape.*—Roughly ovate, asymmetric.

*Petal apex shape.*—Cuspidate, asymmetrical.

*Petal base shape.*—Fused.

*Petal margin.*—Mainly entire and mildly undulate.

*Petal length, from the corolla opening.*—3.5 cm.

*Petal width, maximum.*—3.2 cm.

*Corolla, texture of upper surface.*—Glabrous, papillose.

*Corolla, texture of lower surface.*—Glabrous, papillose.

*Pedicel, color.*—Green, RHS 144B, some anthocyanins present.

*Length.*—2.1-2.7 cm.

*Diameter.*—0.25 cm.

*Pedicel, texture.*—Smooth, glabrous.

Calyx:

*Form.*—5 sepals, closely attached to the base of the flower.

*Color, visible outer surface.*—RHS 145C.

*Length.*—1.0-1.2 cm.

*Width.*—0.4 cm.

*Shape.*—Subulate.

*Apex shape.*—Acute.

*Base.*—Fused.

*Margins.*—Entire.

*Texture, upper surface.*—Glabrous

Reproductive organs:

Gynoecium:

*Pistil.*—1, with a 5-lobed stigma.

*Style length.*—1.8 cm.

*Diameter*.—0.05 cm.
*Style color*.—RHS 150C.
*Stigma color*.—RHS 144B.
*Stigma shape*.—Five lobed.
*Ovary color*.—RHS 144B.

Androecium:

*Stamens*.—5, surrounding the style and stigma.
*Filaments*.—Fused with the base of the flower.
*Anther*.—Elongated.
*Anther color*.—RHS 158A.
*Anther length*.—1.0 cm.
*Color of pollen*.—RHS 4D.
*Pollen amount*.—Moderate.

Fertility/seed set: Has not been observed on this hybrid.

Disease/pest resistance: Has not been observed on this hybrid.

What is claimed is:

1. A new and distinct variety of *Mandevilla* plant named 'MANZ0023', substantially as illustrated and described herein.

* * * * *